United States Patent [19]

Ruderian

[11] Patent Number: 4,597,757
[45] Date of Patent: Jul. 1, 1986

[54] HEAT AND SALVE APPLICATOR

[76] Inventor: Max J. Ruderian, 545 Hanley Ave., W. Los Angeles, Calif. 90049

[21] Appl. No.: 757,381

[22] Filed: Jul. 22, 1985

[51] Int. Cl.$^4$ ............................................. A61M 7/00
[52] U.S. Cl. ..................................... 604/291; 128/399
[58] Field of Search ................ 604/291; 128/399, 368, 128/402

[56] References Cited

U.S. PATENT DOCUMENTS

| | | | |
|---|---|---|---|
| 2,081,034 | 5/1937 | Carter | 604/291 |
| 2,706,988 | 4/1955 | Weber | 128/402 |
| 2,787,998 | 4/1957 | Grossi et al. | 604/291 |

*Primary Examiner*—John D. Yasko
*Attorney, Agent, or Firm*—Pastoriza, Kelly & Lowry

[57] ABSTRACT

The applicator comprises a portable hand-held blower including a fan, a motor and heating wires to provide a stream of heated air out of an exhaust opening. A porous support element may cover the exhaust opening. A fabric material can be arranged to be draped about the motor housing in hooded fashion. Another fabric is arranged about the porous support element to provide a cushioned surface for engaging a body portion. This latter fabric material is impregnated with a medicant so that the heated air from the blower opens up the pores of the skin of a portion of the human body engaged by the fabric. The medicant is then easily absorbed thereby bringing relief to victims of arthritis and other aches and pains. The hood keeps the hot air generated by the blower in proximity to the body portion.

5 Claims, 3 Drawing Figures

HEAT AND SALVE APPLICATOR

RELATED APPLICATIONS

This application contains a portion of the disclosure of co-pending application Ser. No. 06/701,745, filed Feb. 14, 1985, for Salve Applicator.

FIELD OF THE INVENTION

This invention relates to noninvasive treatments for muscular or other soreness, and more particularly to an improved applicator for applying salve-like medicants and/or heat and pressure to a body portion for relieving aches and pains.

BACKGROUND OF THE INVENTION

Many salves are available on the market sometimes in semi-viscous form or even liquid form for rubbing over body portions to relieve aches and pains. Usually the salve is applied by using a cotton swab or gauze pad and simply manually rubbing the medicant into the pores of the skin on the body portion afflicted. The medicant itself often provides a soothing effect and the effect of heating the area involved.

Further, applicators are provided to assuage aches and pains by heat or massage. However, heat is not retained in the vicinity of an area to be massaged.

BRIEF DESCRIPTION OF THE PRESENT INVENTION

The present invention has to do with an applicator for heat or salve which retains heat and, at the same time, provides a massaging motion. The same thus relieves aches and pains. A stream of heated air is provided which is directed at the body portion afflicted thereby enabling a medicant to be more readily absorbed. A hood is used as part of the applicator to keep the heated air from escaping.

The hood acts as a shroud not only for the applicator body, but also for the human body portion.

According to another feature of the present invention, means are provided to cause the hood to fit snugly around the applicator body and thereby to prevent the escape of heated air upwardly between the applicator body and the hood.

Another feature of the invention resides in a porous support element positioned adjacent to the exhaust opening. A fabric material covers this support element to provide a cushioned surface for application to a body portion. The heated air from the exhaust opening and engagement of the cushioning surface functions to heat the area and soothe the body portion.

A salve or medicant is impregnated within the fabric material so that the same is readily transferred to the body portion through the skin pores under influence of the heated air stream.

In some embodiments of the invention, the casing includes a vibrating element which will aid in moving the cushioned surface over the afflicted body portion area to be treated.

BRIEF DESCRIPTION OF THE DRAWINGS

A better understanding of this inventin will be had by now referring to the accompanying drawings in which.

DETAILED DESCRIPTION OF THE INVENTION

Figure 1:
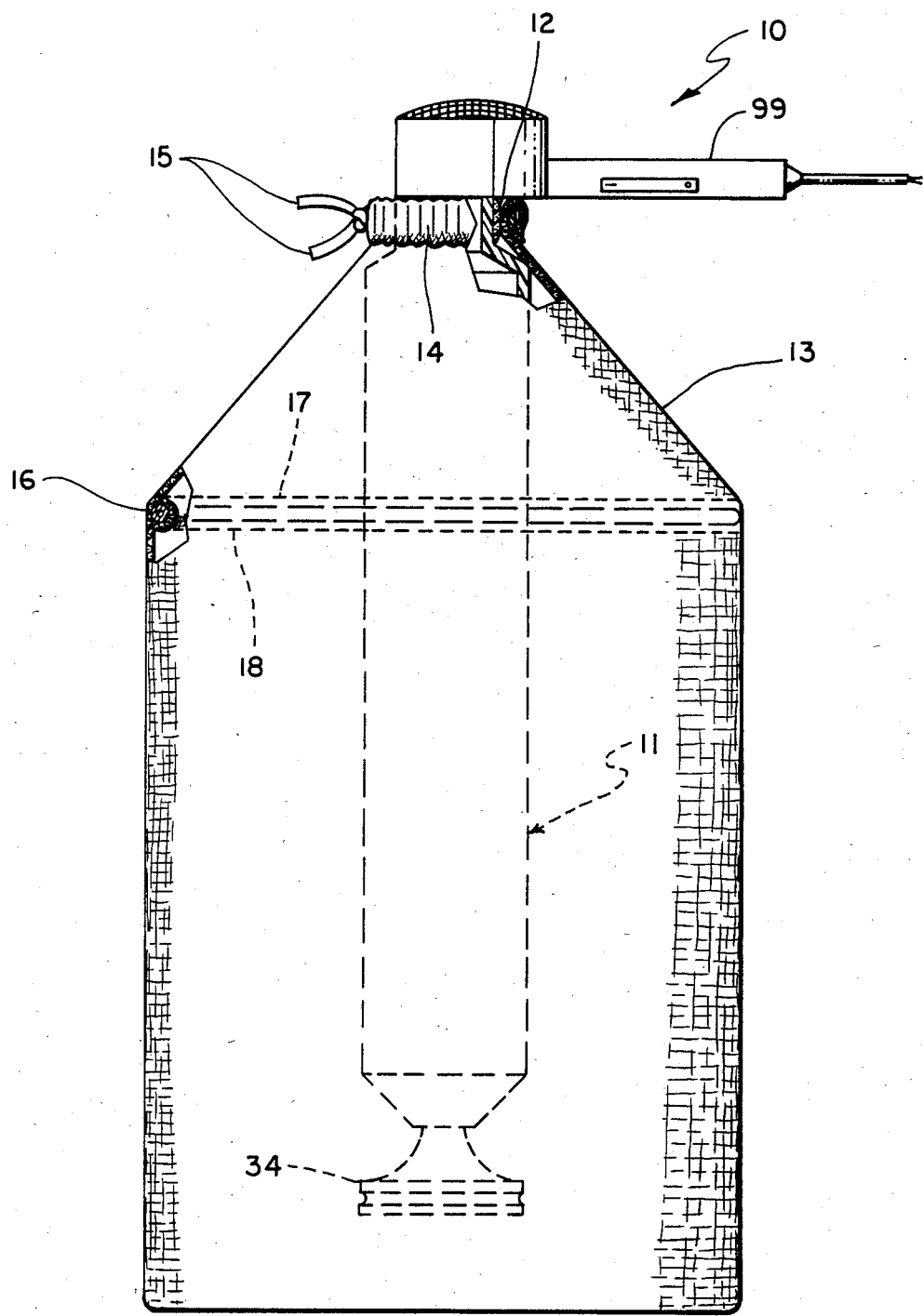
FIG. 1 is a vertical elevational view, partly in section, of a heat and salve applicator constructed in accordance with the present invention.
Figure 2:
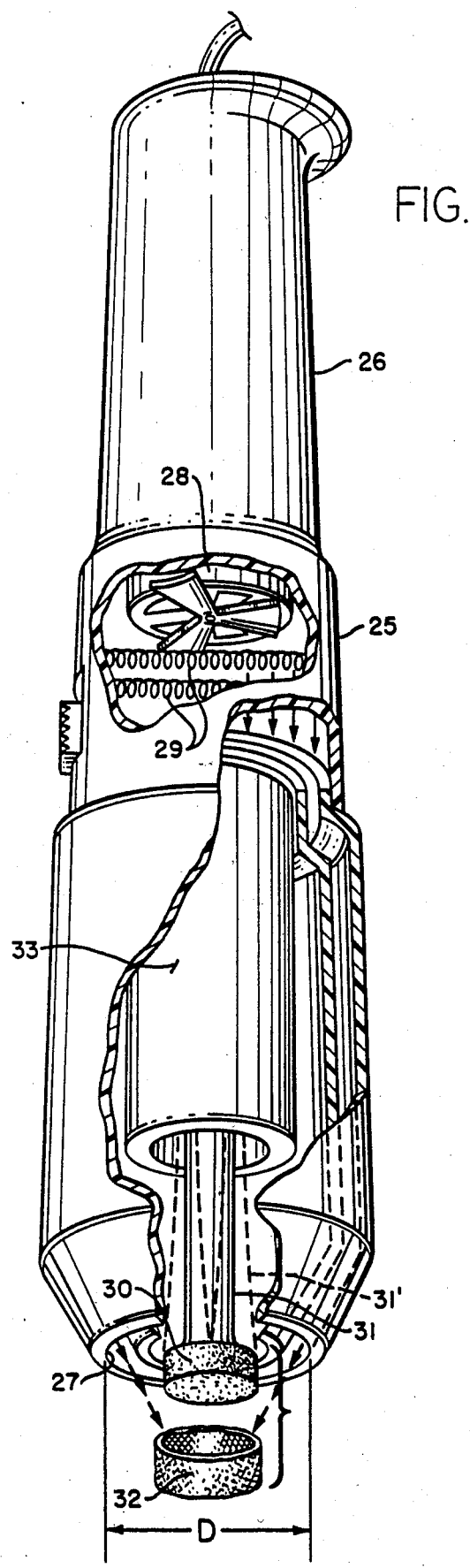
FIG. 2 is a broken-away perspective view of apparatus constructed in accordance with the invention.

In the drawings, in FIG. 1, a heat and salve applicator is shown at 10 including an approximately cylindrical body 11 which may be similar to or identical to that shown in FIG. 2.

Body 11 has a foam rubber ring 12 fixed therearound. A fabric hood 13 is suspended from body 11. Hood 13 is gathered at 14 and has a drawstring 15 which ties the gathered portion 14 around foam rubber ring 12.

Note will be taken that foam rubber ring 12, gathered portion 14 and drawstring 15 prevent air blown into the interior of hood 13 from escaping upwardly between hood 13 and body 11.

A copper tube 16 is sewn into the hood 13 at 17 and 18 to keep the lower portion of the hood 13 spread out to form a cylinder and encompass a body portion.

Referring now to FIG. 2, an applicator body is shown including a casing 25 with a handle 26. Handle 99 in FIG. 1 may be substituted for handle 26 if desired. The casing includes at its lower end as shown in FIG. 2, a lower annular conical exhaust opening 27 for heated air. This heated air is provided by a blower including a fan motor 28 incorporated in the casing 25 and heating wires 29.

In the central portion of the exhaust opening 27 for the heated air, there is a sponge-like porous support element 30 detachably secured to the end of a shaft 31. A fabric material 32, in turn, is shown exploded away from the element 30. This fabric can be impregnated with a medicant M. Shaft 31 actually constitutes the vibrating element of a vibrator 33 centrally positioned in the overall casing structure.

In the embodiment of FIG. 2, the heated air will heat the skin area surrounding the fabric 32, the exhaust opening 27 focusing the airflow onto the body portion. The fabric can then be placed into engagement with a heated skin area and the medicant will be absorbed. The vibrator can be actuated to orbit the shaft and between the phantom line position 31' thereby massaging the skin and aiding absorption. By holding the applicator in a manner so that the fabric is spaced away from the area, only the heated air will treat the area and the application of air alone might be sufficient to bring relief. In this latter event, the vibratior would not be used. When the vibrator is used, the porous support element will orbit and intercept some of the heated air from the exhaust opening 27 so that this air will pass through the fabric and help in absorption of the medicant.

Figure 3:
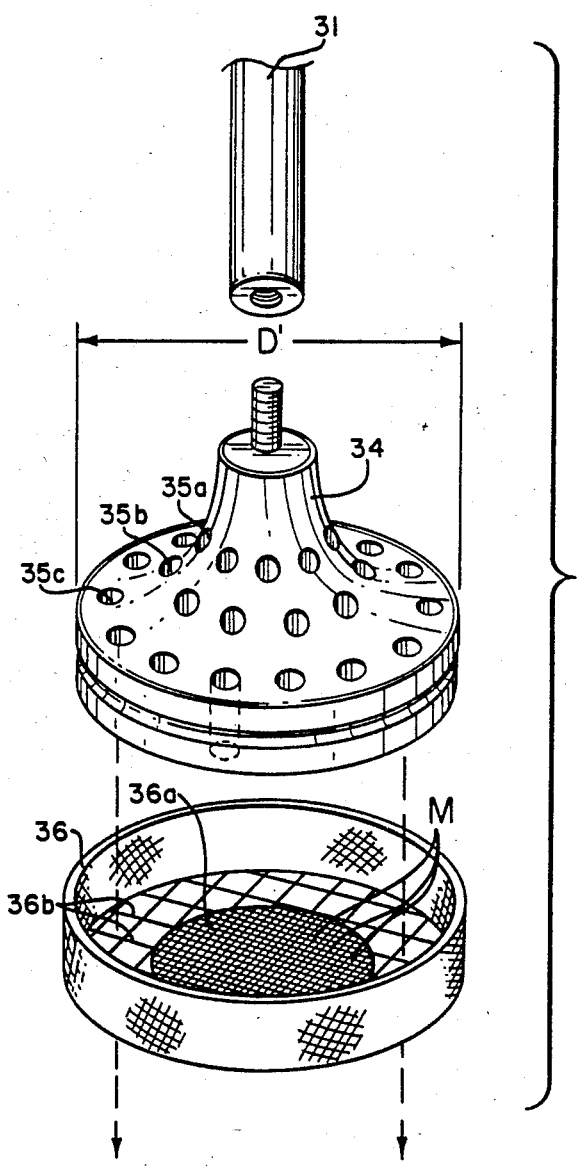
FIG. 3 is an exploded view of preferred substitute components for use in the embodiment of FIG. 2.

FIG. 3 illustrates the manner in which the preferred support element somewhat larger than the support element 30 of FIG. 2 can be substituted together for a larger fabric of unique construction.

More particularly, a larger support element is shown at 34 and, in this instance, rather than a sponge-like element, constitutes a hollow plastic housing with circular rows of vertical openings 35a, 35b and 35c passing therethrough and out the bottom.

Shown exploded below the support element 34 is a fabric material 36 of cup shape to fit over and be held frictionally by the support element 34. Fabric 36 may be impregnated with a medicant M. It will be noted that the fabric has a dense central portion 36a the peripheray of which is supported by a less dense or almost net-like fabric material 36b.

Referring back to FIG. 2, if the outside diameter of the exhaust opening for the hot air is D, then by making the outside diameter D' of the support element 34 the same as or greater than D, the periphery of the support and fabric will overlie the exhaust opening so that heated air will pass through the openings 35a, 35b and 35c and thence through the fabric 36. In this respect, however, air from the outer row of openings 35c will pass through the net support part of the fabric 36b directly onto the body portion being treated while air through the openings 35a and 35b will pass through the dense portion of the fabric 35a to help in absorption of the medicant.

As shown in FIG. 3, the support element 34 is detachably secured to the shaft 31 as by a screw and tapped opening in the end of the shaft. While either the porous sponge-like support 30 or the larger plastic housing support 34 can be used on the end of the shaft 31, in the preferred embodiment, the support 34 is used to provide for the most satisfactory all-around use.

SUMMARY

The use of the hood 13 makes possible heat application to a portion of the human body without unnecessary heat loss. Further, heat loss at the top of hood 13 is prevented by the tight fit of foam rubber ring 12 on body 11, and the tight fit with which gathered portion 14 of hood 13 may be assured by pulling and tying drawstring 15 in the position shown.

It is another outstanding feature of the invention that heat and/or salve may be applied to a body portion while a massage is made possible and also while use is made of hood 13 to keep the body portion warm. In the latter case, hood 13 is used to cover the body portion.

Note will be taken that the embodiment of the invention shown in FIG. 1 may be used with or without salve, etc., and with or without a vibrator. Salve and a vibrator may also be used together or separately.

Other changes falling within the scope and spirit of this invention will occur to those skilled in the art. The heat or salve applicator is therefore not to be thought of as limited to the specific embodiments set forth for illustrative purposes.

What is claimed is:

1. A heat and salve applicator comprising:
    a hollow approximately cylindrical applicator body to be held with its axis extending somewhat in a vertical direction,
    said body having an upper air intake opening and a lower air exhaust opening;
    heating means in said applicator body;
    a fan mounted within said applicator body above said heating means to establish a flow of air into said upper intake opening, through said heating means and out of said lower exhaust openings;
    a hood comprising an approximately cylindrical piece of cloth; and
    means sealing said hood around the exterior of said appliator body below but adjacent to said upper intake opening, said sealing means including a foam rubber ring around said applicator body,
    a drawstring at the top of said cloth to hold said hood in engagement with said applicator body, and
    a rigid ring substantially larger than the diameter of said applicator body sewn into said cloth in a position spaced from said drawstring to cause said cloth to spread out over said applicator and a body portion to be treated.

2. The invention as defined in claim 1, wherein:
    a vibrating element is incorporated in said body for vibrating the applicator and thereby facilitating the absorption of medicant into the pores of the body portion.

3. The invention as defined in claim 1, wherein:
    a vibrating element is incorporated in said body for vibrating the applicator and thereby facilitating the absorption of medicant into the pores of the body portion.

4. A heat and valve applicator comprising:
    a hollow approximately cylindrical applicator body to be held with its axis extending somewhat in a vertical direction, said body having an upper air intake opening and a lower air exhaust opening;
    heating means in said applicator body;
    a fan mounted within said applicator above said heating means to establish a flow of air into said upper intake opening, through said heating means, and out of said lower exhaust opening;
    a vibrator mounted within said applicator body and including an externally exposed vibratory massage element positioned substantially at said lower exhaust opening whereby the flow of air passing out of said lower exhaust opening flows directly around and about said vibratory element; and
    a flexible hood fixed around the exterior of said applicator body below but adjacent to said upper intake opening in a manner to be suspended therefrom, said hood having a lower end disposed below said lower exhaust opening and said vibratory massage element.

5. The invention as defined in claim 4, wherein:
    said hood is made of a cloth material, and means are provided to spread said cloth away from said body in the region of said lower exhaust opening and said vibratory massage element.

* * * * *